United States Patent [19]
Wise

[11] Patent Number: 5,254,465
[45] Date of Patent: * Oct. 19, 1993

[54] PROCESS FOR MANUFACTURE OF ALKALINE EARTH ACETATES

[75] Inventor: Donald L. Wise, Belmont, Mass.

[73] Assignee: Northeastern University, Boston, Mass.

[*] Notice: The portion of the term of this patent subsequent to Nov. 26, 2008 has been disclaimed.

[21] Appl. No.: 770,978

[22] Filed: Oct. 1, 1991

Related U.S. Application Data

[63] Continuation-in-part of Ser. No. 369,183, Jun. 20, 1989, Pat. No. 5,068,188.

[51] Int. Cl.$^5$ .................... C12P 7/54; C12P 39/00; C12P 7/40; C12N 1/20
[52] U.S. Cl. ................ 435/140; 435/252.7; 435/136; 435/42; 435/842
[58] Field of Search ............ 435/140, 252.7, 136, 435/42, 842

[56] References Cited

U.S. PATENT DOCUMENTS

| | | | |
|---|---|---|---|
| 4,009,075 | 2/1977 | Hoge | 435/162 |
| 4,211,647 | 7/1980 | Friedman et al. | 210/17 |
| 4,275,163 | 6/1981 | Gallo | 435/209 |
| 4,334,026 | 6/1982 | Chynoweth et al. | 435/163 |
| 4,342,836 | 8/1982 | Harvey | 435/316 |
| 4,379,844 | 4/1983 | Young | 435/251 |
| 4,400,470 | 8/1983 | Zeikus et al. | 435/162 |
| 4,405,717 | 9/1983 | Urbas | 435/140 |
| 4,447,530 | 5/1984 | Young | 435/68 |
| 4,472,504 | 9/1984 | Gallo | 435/209 |
| 4,587,218 | 5/1986 | Hershberger | 435/253 |
| 4,588,688 | 5/1986 | Maxwell | 435/142 |
| 4,636,467 | 1/1987 | Chynoweth | 435/842 |
| 4,643,972 | 2/1987 | Young | 435/252 |
| 4,644,060 | 2/1987 | Chou | 536/30 |
| 4,657,863 | 4/1987 | Maxwell et al. | 435/142 |
| 4,686,189 | 8/1987 | Redikultsev et al. | 435/289 |
| 4,713,336 | 12/1987 | Srinivasan et al. | 435/155 |
| 4,722,741 | 2/1988 | Hayes et al. | 48/197 A |
| 4,732,680 | 3/1988 | Weaver et al. | 210/610 |
| 4,734,368 | 3/1988 | Schindler | 435/145 |
| 4,735,724 | 4/1988 | Chynoweth et al. | 210/603 |
| 4,795,101 | 1/1989 | Silver | 241/12 |
| 5,068,188 | 11/1991 | Wise et al. | 435/140 |

OTHER PUBLICATIONS

Wise, Donald L. and Don C. Augenstein, "An Evaluation of the Bioconversion of Woody Biomass to Calcium Acetate Deicing Salt", *Solar Energy*, 41:5, 453-463, (1988).

Wise. D. L. and D. Augenstein, Proceedings of the 1988 Annual Meeting of the American Solar Energy Society, Inc., Cambridge, Mass., Jun. 20-24, 1988, pp. 36-46.

*Primary Examiner*—David M. Naff
*Assistant Examiner*—L. Blaine Lankford
*Attorney, Agent, or Firm*—Weingarten, Schurgin, Gagnebin & Hayes

[57] ABSTRACT

A process for the manufacture of alkaline earth salts of acetic acid. Biomass is fermented under appropriate conditions to produce acetic acid, which is extracted from the fermentation broth with the aid of a basic liquid ion exchanger dissolved in an organic phase. The organic phase containing the product acetic acid is then reacted directly with a basic material such as limestone, and the resulting alkaline earth acetate product is recovered from the aqueous phase.

12 Claims, 1 Drawing Sheet

PROCESS FOR MANUFACTURE OF ALKALINE EARTH ACETATES

RELATED APPLICATION

This application is a continuation-in-part of application Ser. No. 07/369,183, filed on Jun. 20, 1989, now U.S. Pat. No. 5,068,188.

FIELD OF THE INVENTION

This invention relates to deicing materials, and more particularly, to a method for producing alkaline earth acetates by fermentation of organic wastes.

BACKGROUND OF THE INVENTION

Commonly used sodium chloride road salt is environmentally damaging. It is corrosive to roads, bridges, and vehicles using them; it is harmful to roadside vegetation; it pollutes aquatic habitats and drinking water supplies; and it damages underground cables, among other effects. Although this material is relatively inexpensive, when one considers the damage it causes, it is clear that the true cost of its use is in fact quite high.

The acetates of calcium and magnesium have been suggested as non-polluting and non-corrosive replacements for sodium and calcium chloride for road applications, but these materials are presently in somewhat limited supply and the present manufacturing processes render them too expensive for such applications. Hence it would be very desirable to have a low cost process for producing calcium and magnesium acetates from readily available cheap starting materials. Such a process is the subject of this application.

SUMMARY OF THE INVENTION

In the present invention, acetic acid is produced inexpensively from fermentable organic wastes, thus converting a community waste into a resource, with the additional benefits of reducing waste disposal problems and costs, and reducing ground water pollution from landfills. It is subsequently converted to one or more alkaline earth metal acetates, which can be substituted for the environmentally troubling common road salt sodium chloride presently in use, and also for other purposes.

Significant economies are achieved by using organic wastes as the starting materials, employing a relatively inexpensive extraction operation instead of a more energy-intensive distillation to separate the acetic acid product from the fermentation broth, and by forming the final product in a single treatment step with the aid of relatively inexpensive and locally available limestone-type materials to recover acetic acid from the extracting medium and simultaneously convert it to the desired products.

The process for producing alkaline earth salts of acetic acid includes the steps of fermenting biomass anaerobically in a continuous manner to form acetic acid; extracting the acetic acid continuously from the fermentation broth with the aid of a liquid ion exchanger, which results in the production of an organic phase containing acetic acid complexed with the ion exchange material; and treating the organic phase containing the acetic acid continuously and directly with a solid basic material containing at least one type of alkaline earth metal ion, which results in the formation of at least one alkaline earth salt of acetic acid and water, and in simultaneous regeneration of the ion exchange material. The alkaline earth acetate salt, located substantially in the aqueous phase, is finally recovered as a solid or as a concentrated aqueous solution.

DESCRIPTION OF THE DRAWING

The invention will be more completely understood from a consideration of the following detailed description taken in conjunction with the drawing; in which.

DETAILED DESCRIPTION

Figure 1:
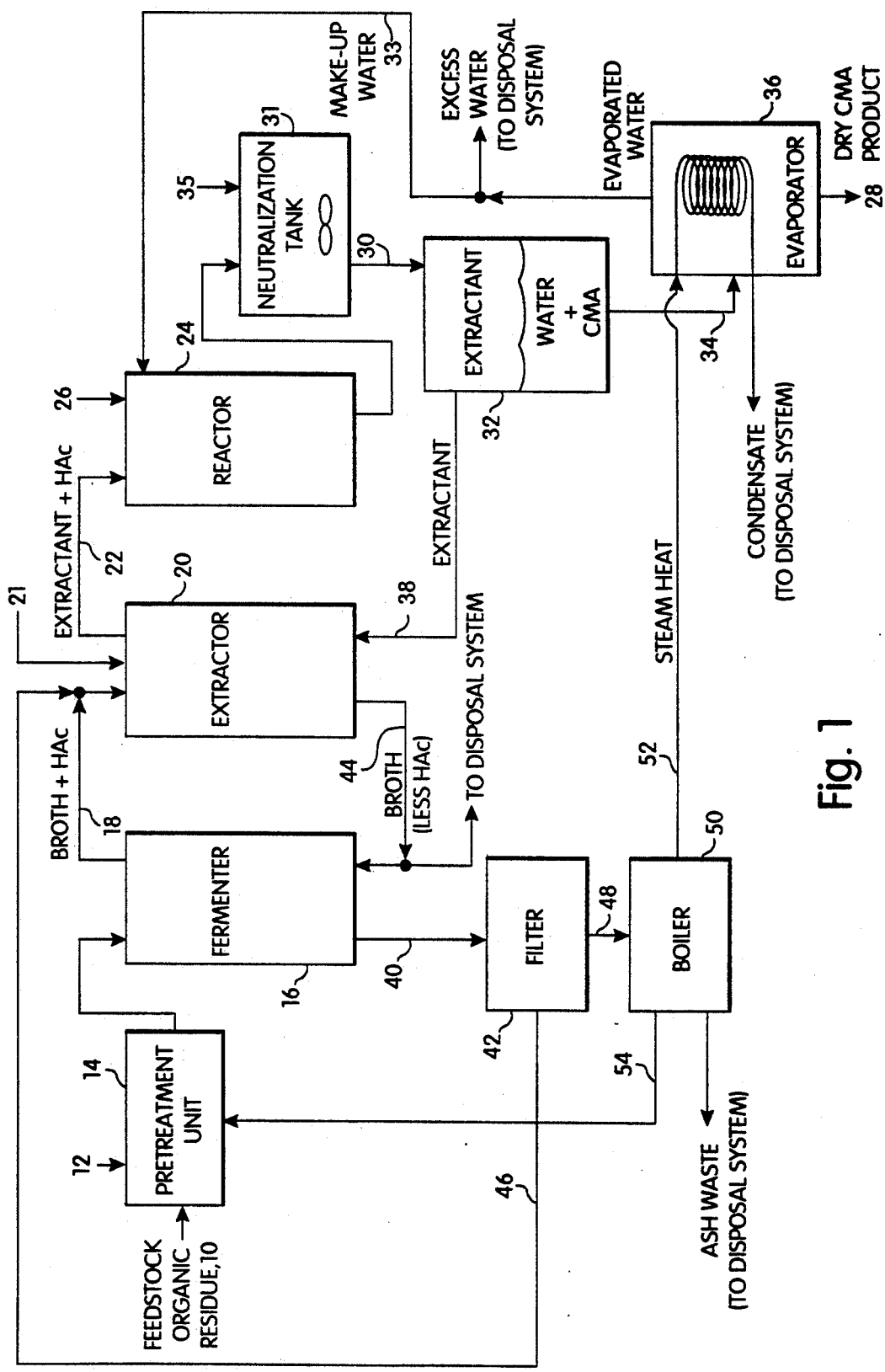
FIG. 1 shows equipment and material flows for the process of the invention.

As shown in FIG. 1, the process for producing alkaline earth acetates employs a biomass feed 10, which is treated as may be necessary by reagents 12 in an optional pretreatment operation 14, and then fermented anaerobically by acetic acid-forming microorganisms in a fermenter 16 to produce dilute acetic acid solution, typically at a concentration of about 0.5-3.5%. This is transferred via line 18 to extractor 20, where acetic acid is extracted from the fermentation broth with the aid of an extracting medium 21 containing organic solvent and a liquid ion exchanger. The resulting organic phase, typically containing approximately 0.1-1.01 N acetic acid plus approximately 10% liquid ion exchanger, the remainder being an oil phase such as kerosene, is transferred via line 22 to a reactor 24 where it is treated directly with an alkaline earth-containing basic material 26 to recover the acetic acid from the organic phase and simultaneously convert it to the desired alkaline earth acetate product 28. At this point in the process, product 28 is located primarily in the aqueous phase.

The organic and aqueous phases from the reactor 24 may optionally be transferred to neutralization tank 31, where any unreacted acetic acid carried over from the reactor 24 may be utilized completely thereby enhancing the production of desired alkaline earth acetate product 28. In neutralization tank 31, the pH is raised to about pH 8 and a small amount of hydrated lime (Ca(OH)$_2$ or Mg/Ca(OH)$_2$) 35 is added to react substantially all of the previously unreacted acetic acid. This reaction may alternatively take place directly in the settling/separation tank 32.

The organic and aqueous phases from neutralization tank 31 are transferred via line 30 to settling/separation tank 32, where they are separated, and the aqueous phase which contains the product alkaline earth acetate is conveyed via line 34 to the evaporator 36 or other suitable device for removal of the water. The water removed from the evaporator may be recycled back to the reactor via line 33 to provide additional water as needed to promote the desired reaction and facilitate material handling.

The separated organic phase containing the organic solvent and liquid ion exchanger is recycled to extractor 20 via line 38. A portion of the aqueous phase from extractor 20 is conveyed to fermentor 16 via line 44 and a portion is sent to waste. The solids from fermenter 16 including any acetic acid-containing fermentation broth which may be carried along, is conveyed via line 40 to a filter 42. The filtered acetic acid-containing fermentation broth is recycled via line 46 to the extractor. After being filtered, the fermenter solids are conveyed via line 48 to boiler 50 where they are burned to produce steam and hot air. The steam heat at about 600° C. is conveyed to the evaporator via line 52. Some portion of the steam may also be conveyed via line 54 to the pretreatment unit to provide steam injection when necessary.

Biomass feed 10 may be any of a wide variety of organic waste materials. Among these are woody biomass such as forest residues which are not suitable for lumber or paper pulps, sewage sludge residues, municipal solid waste, corn products such as wet-milled corn liquor or corn steepage, animal manure and selected industrial organic waste such as paper manufacture waste, and whey such as from cheese processing. Ample supplies of each of these materials exist, at low cost. In some cases, the suppliers of the biomass might even be willing to pay the user to take their waste material. Primary biomass sources such as corn or wood from trees such as poplar can also be used, though at higher cost.

Other suitable feedstocks include fossil fuels such as coal, bituminous, and especially sub-bituminous, lignite and peat.

Pretreatment step 14 is optional, and is employed as and if needed to enhance fermentation to acetic acid. Those skilled in the fermentation art will know which biomass feed materials require pretreatment before the fermentation operation, and the sorts of treatment to be applied. Easily fermented biomass such as whey or wet-milled corn requires no pretreatment. Biomass fermented with difficulty such as woody biomass material will generally require a more intense pretreatment such as the application of steam or alkali. For example, wood chips may be heated under pressure to temperatures of about 125° C.–150° C. Sewage sludge may be benefited by mild treatment by acid, base, or steam to facilitate ready fermentation to acetic acid. For example, sewage sludge may be heated under pressure to a temperature of about 125° C. Fossil fuels, such as lignite may be pretreated at 150° C.–175° C. using a steam injection process as is known in the art.

It is preferable to carry out the fermentation operation using a mixture of hardy acclimatized microorganism strains adapted to utilize the feedstock of interest so that sterilization of the feedstock is not required. Mixtures of anaerobes are obtainable from the rumen of ruminant animals and from the anaerobic digesters of municipal sewage treatment plants, the latter being preferred for practical purposes. A starter inoculum is obtained from a working municipal anaerobic digester operating on a sewage sludge feed. This is introduced into a small continuous reaction such a chemostat operating at about 37° C. (i.e., mesophilic conditions) and employing the feedstock of interest as a carbon source. The pH is lowered to about 5-6 so that methane-forming organisms are washed out and organic acid-forming microorganisms become dominant which yield acetic acid plus small amounts of other carboxylio acids of higher molecular weight. The temperature of the fermentation is then raised to about 60° C. and the microorganisms are allowed to acclimatize themselves under these thermophilic conditions. Acetic acid-producing microorganisms such as *Clostridium thermoaceticum* and other acetic acid-producing organisms surviving from the municipal anaerobic digester are dominant under these conditions. This fermenting material is used in turn as an inoculum for the full scale fermentation to produce acetic acid.

Fermenter 16 is any unit which is appropriate for the fermentation of the particular biomass feed 10 which is to be employed in the process, as will be known by those skilled in the art. A "packed-bed" fermenter is preferred for most "solid" materials such as woody biomass. A conventional continuous stirred tank reactor may be preferred for sewage sludge fermentation, while a high-rate anaerobic filter or fixed film type fermenter may be most useful for soluble materials such as whey or a material that is solubilized by pretreatment.

The fermentation operation is preferably carried out under thermophilic conditions, at about 60° C., employing the bacterium *Clostridium thermoaceticum*, as may be selected from a working anaerobic digester, as described above. Fermentation studies using thermophilic anaerobic conditions have indicated that the concentration of organic acids in such a fermentation reaction reaches from about 0.5% to 3.5%, at the maximum, with the acetic acid being predominant and the higher carboxylic acids being produced in significantly smaller quantities.

The extraction step occurring in extractor 20 employs a low to medium polarity organic solvent containing a liquid ion exchanger. Examples of suitable organic solvents are toluene, kerosene, and cyclohexane. A preferred solvent is kerosene, which has the advantage of being inexpensive and has no deleterious effect on the microorganisms. The liquid ion exchanger is preferably an organic base such as trioctylphosphine oxide (TOPO) or an organic amine such as the material "ADOGEN 283-D" (TM), a branched ditridecylamine. Other examples are listed in Table I below. The liquid ion exchanger material is typically employed at a level between 2 to 15% in the organic solvent.

Where the biomass feed 10 may contain heavy metals, for example, where the feed is sewage sludge, the liquid ion exchanger selected is one which will not convey such heavy metals into the extraction medium by complexation or otherwise. Ideally, no heavy metals are removed from the fermentation broth in the extraction step, but in practice small amounts of heavy metals may carry over into the acetic acid-containing extract. These are of limited concern so long as their levels in the final product are sufficiently low. In those cases in which heavy metals may be a concern, it is a simple matter to test the acetic acid-containing extract and/or the final product for their presence and levels. If an objectional level of heavy metals is found in such a test, a different liquid ion exchanger is employed or the conditions of the extraction step are changed, so that heavy metal contamination of the product is minimized.

On the other hand, the extraction step may be operated to actually remove heavy metals from the fermented sewage sludge. In this case, a separate step (not shown) is used to precipitate the heavy metals, thus removing them from the system.

Following extraction of the acetic acid from the aqueous product stream, the organic and aqueous phases are separated. The organic phase, now rich in acetic acid complexed with ion exchanger material, is treated directly in reactor 24 with a basic calcium- and/or magnesium-containing substance such as calcium oxide, limestone (calcium carbonate), magnesite (magnesium carbonate), or dolomite (calcium magnesium carbonate) which is capable of reacting with acetic acid to form acetate salts and water. These basic alkaline earth-containing substances are preferably obtained locally, and are used in a crushed, ground or powdered state.

The reaction between the acetic acid and the base is quantitative and reasonably rapid. The acid may be directly treated with sufficient water to promote the desired reaction and to facilitate material handling. Any additional water may be added to reactor 24 as needed. The reaction regenerates the extractant ion exchange material, which is recycled, and simultaneously produces an aqueous solution of the desired water soluble acetate salt or salts.

The reaction illustrating the product formation reaction, written for dolomite, is:

$$4 Ex\bullet HAc + CaMg(CO_3)_2 \; H_2O$$
$$4Ex + CaMgAc_4 + 2CO_2 + 2H_2O$$

in which the abbreviation Ex stands for the extractant, namely, the basic oil-containing ion exchanger. In practice, a slight deficiency of the basic alkaline earth-containing material is generally employed, so that it is essentially completely consumed in the reaction, thereby promoting formation of a liquid system for ease of processing.

The relative amounts of the alkaline earth metals in the product are determined by the composition of the base used to react with the acetic acid. If particular ratios of the alkaline earth metal ions are desired in the final product, mixtures of different alkaline earth containing carbonates are employed, the respective materials and their relative amounts being determined by the relative percentages of the alkaline earth metal ions desired for the final product.

The alkaline earth acetates which are the products of the invention are used primarily as deicing materials to replace the presently used road salts, and secondarily may have applications in processes to remove sulfur dioxide from gaseous streams, and as additives to fossil fuels to enhance combustion.

EXPERIMENTAL

Extraction of Acetic Acid

Extractants investigated include long chain alphatic secondary and tertiary amines with low water solubilities, as well as a basic phosphine oxide. These are identified by trade name, chemical composition and chemical type in Table I.

TABLE I

| Extractant | Extractants Investigated Chemical Composition | Type |
|---|---|---|
| ADOGEN 283-D[1] | di-tridecyl amine, branched | secondary amine |
| AMBERLITE LA2[2] | highly branched sec. amine | secondary amine |
| ADOGEN 381[1] | tri-isooctyl amine | tertiary amine |
| ALAMINE 336[3] | tri-$C_8$, $C_{10}$ st. chain amine | tertiary amine |
| TOPO[4] | tri-n-octyl phosphine oxide | Basic Phasphine Oxide |

[1]Ashland Chemical
[2]Rohm and Haas
[3]Henkel
[4]American Cyanamid

Equilibrium Constants for Extraction of Acetic Acid

Equilibrium constants for the extraction process were determined, as these are a more satisfactory measure than the conventionally reported distribution coefficients. A series of liquid ion exchange materials (extractants) dissolved in kerosene were used to extract 3% aqueous acetic acid solutions. The process for the formation of the extractant-acetic acid adduct is described by the following equation:

$$HAc(aq) + Ex(org) \rightleftharpoons Ex\bullet HAc(org)$$

where HAc=acetic acid and Ex=extractant. $K_{eq}$ is defined:

$$K_{eq} = \frac{[ExHAc](org)}{[HAc](aq)[Ex](org)}$$

where quantities in square brackets indicate the molar concentrations at equilibrium. Each phase (aq. and organic) was titrated with sodium hydroxide solution to determine the efficiency of extraction and from these data equilibrium constants for the extraction were determined.

The equilibrium constant for the extraction of acetic acid (HAc) by tri-n-octyl phosphine oxide (TOPO) was investigated over a four-fold variation in the initial [HAc]/[TOPO] ratio. In that range a standard deviation from the norm of 21.2% was observed with no discernable trend in results. Results for this series of experiments as reported in Table 2.

TABLE 2

| $K_{eq}$ for Extraction of HAc by TOPO | |
|---|---|
| [HAc]/[TOPO] | $K_{eq}$ |
| 0.60 | 6.19 |
| 1.20 | 5.00 |
| 1.20 | 7.05 |
| 1.25 | 8.78 |
| 2.00 | 5.13 |
| 2.40 | 8.17 |
| Mean 6.720 ± 1.427 ($\sigma$) | |

$K_{eq}$ values for the several extractants studied are shown in Table 3. The two most preferred extractants are TOPO ($K_{eq}$=6.72) and ADOGEN 283-D ($K_{eq}$=31.5).

TABLE 3

| $K_{eq}$ For Extraction of HAc By Various Extractants | |
|---|---|
| Extractant | $K_{eq}$ |
| TOPO | 6.72 ± 1.4% (six trials) |
| ADOGEN 283-D | 31.5 |
| ADOGEN 381 | 0.15 |
| ALAMAME 336 | 0.42 |
| AMBERLITE LA-2 | 2.62 |

Formation of Alkaline Earth Acetates

The recovery of HAc from the extractant by direct reaction of Ex•HAc in the organic phase with calcium hydroxide, magnesium hydroxide, calcium carbonate, magnesium carbonate, and dolomitic limestone was studied. In the later case, stoichiometric quantities of dolomite were dissolved with evolution of carbon dioxide, leaving only a slight insoluble residue which could not be dissolved in hydrochloric acid. (In a separate experiment recovery of insoluble material left after solution of dolomite in hydrochloric acid indicated that dolomite was 93.4% $CaMg(CO_3)_2$ which is in accord with the reported carbonate content of 90–95%). In the reaction of the adduct (Ex HAc) with dolomite ($CaMg(CO_3)_2$) the reaction products are only regenerated extractant, calcium magnesium acetate (CMA), water, and carbon dioxide. The latter escapes as a gas, and the water is useful for solubilizing the product to aid its separation from the extractant.

As illustrated in Table 4, in one experiment dolomite was converted to acetate salt in 36.5% yield in 5 minutes. Longer contact time between the dolomite and the acetic acid rich organic phase resulted in complete conversion.

Native dolomite was reacted directly with the organic phase containing TOPO•HAc. A solution (25 ml) of 0.50M HAc was shaken with 50 ml of TOPO dissolved in kerosene (0.25M). The clear organic phase containing the TOPO HAc adduct was removed and to this was added crushed dolomite in excess of the stiochiometric quantity required. In several trials the organic layer was shaken with the dolomite for varying periods of time. The unreacted dolomite was recovered, washed, dried and weighed and from this was calculated the percent of the theoretical amount of dolomite which reacted. The results for three trials are summarized in Table 4. In Trial 1, conducted at room temperature, agitation was continued for only 5 minutes, but nevertheless, 37% of the theoretical weight of dolomite reacted. This suggests that contact times of less than an hour will be sufficient for essentially complete reaction. Mechanical agitation was employed in Trials 2 and 3, which were conducted at room temperature and 60° C., respectively. In both cases, the theoretically calculated weights of dolomite reacted. The contact times indicated for Trials 2 and 3 in Table 4 are much longer than required, but clearly demonstrate that quantitative conversion to acetate is quite feasible.

TABLE 4

Reaction of TOPO HAc with Dolomite*

| Trial | Temp | Contact Time | Weight Initial | Dolomite Recovered | Grams Reacted | Percent of Theoretical |
|---|---|---|---|---|---|---|
| 1 | Room Temp | 5 min. | 2.574 | 2.450 | 0.124 | 36.5 |
| 2 | Room Temp | 18 hr. | 2.512 | 2.132 | 0.380 | 111 |
| 3 | 60° C. | 60 hr. | 2.571 | 2.226 | 0.345 | 101.6 |

*Aqueous phase: 25 ml of 0.50 M HAc
Organic phase: 50 ml of 0.25 M TOPO
$K_{eq} = 6.72$
Theoretical weight of dolomite required to react with TOPO HAc = 0.336 g In other experiments calcium hydroxide and calcium carbonate in aqueous slurry were reacted with Ex•HAc in kerosene. After separation of the aqueous phase and removal of any insoluble residue by filtration the dissolved solids were recovered by evaporation and washed with acetone. The product is a white crystalline material.

The white crystals are soluble in water, decompose on heating without melting, and when heated with ethanol and concentrated sulfuric acid give the characteristic odor of ethyl acetate. Moreover, an elemental analysis revealed a material that had the chemical formula of calcium magnesium acetate. This is evidence that the product is the desired acetate salt.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A process for producing calcium and/or magnesium salts of acetic acid comprising the following steps:
    pretreating biomass to facilitate fermentation;
    fermenting the biomass anaerobically in a continuous manner to form acetic acid in a fermentation broth;
    extracting the acetic acid continuously from the fermentation broth with an oil phase which may optionally contain a liquid ion exchanger, resulting in the production of an organic phase consisting essentially of oil, acetic acid and optionally, a liquid ion exchanger material;
    treating the acetic acid-containing organic phase directly and continuously with water and solid basic material containing calcium and/or magnesium metal ions, resulting in the formation of calcium and/or magnesium salt of acetic acid and water, the water forming an aqueous phase, the acetic acid salt being located substantially in the aqueous phase; and
    recovering the calcium and/or magnesium salt of acetic acid from the aqueous phase.

2. The process of claim 1 wherein said pretreating step includes treatment of the biomass by steam injection.

3. The process of claim 1 wherein said pretreating step includes heating the biomass under pressure.

4. The process of claim 1 wherein said pretreating step includes treatment of the biomass with alkali.

5. The process of claim 1 wherein said pretreating step includes treatment of the biomass with acid.

6. A process for producing a calcium salt of acetic acid comprising the following steps:
    fermenting biomass anaerobically in a continuous manner to form acetic acid in a fermentation broth;
    extracting the acetic acid continuously from the fermentation broth with an oil phase which may optionally contain a liquid ion exchanger, resulting in the production of an organic phase consisting essentially of oil, acetic acid and optionally, a liquid ion exchanger material;
    treating the acetic acid-containing organic phase directly and continuously with water and calcium oxide, resulting in the formation of a calcium salt of acetic acid and water, the water forming an aqueous phase, the acetic acid salt being located substantially in the aqueous phase; and
    recovering the calcium salt of acetic acid from the aqueous phase.

7. A process for producing calcium and/or magnesium salts of acetic acid comprising the following steps:
    fermenting biomass anaerobically in a continuous manner to form acetic acid in a fermentation broth, wherein said biomass is selected from the group of fossil fuels consisting of coal bituminous, sub-bituminous, lignite, and peat;
    extracting the acetic acid continuously from the fermentation broth with an oil phase which may optionally contain a liquid ion exchanger, resulting in the production of an organic phase consisting essentially of oil, acetic acid and optionally, a liquid ion exchanger material;
    treating the acetic acid-containing organic phase directly and continuously with water and solid basic material containing calcium and/or magnesium metal ions, resulting in the formation of calcium and/or magnesium salt of acetic acid and water, the water forming an aqueous phase, the acetic acid salt being located substantially in the aqueous phase; and
    recovering the calcium and/or magnesium salt of acetic acid from the aqueous phase.

8. The process of claim 7, further comprising a pretreating step prior to said fermenting step.

9. The process of claim 8, wherein said pretreating step is a steam injection process at temperatures in the range of about 150° C.-175° C.

10. A process for producing calcium and/or magnesium salts of acetic acid comprising the following steps:
fermenting biomass anaerobically in a continuous manner to form acetic acid in a fermentation broth, wherein said biomass is wet milled corn liquor, corn steepage or animal manure;
extracting the acetic acid continuously from the fermentation broth with an oil phase which may optionally contain a liquid ion exchanger, resulting in the production of an organic phase consisting essentially of oil, acetic acid and optionally, a liquid ion exchanger material;
treating the acetic acid-containing organic phase directly and continuously with water and solid basic material containing calcium and/or magnesium metal ions, resulting in the formation of calcium and/or magnesium salt of acetic acid and water, the water forming an aqueous phase, the acetic acid salt being located substantially in the aqueous phase; and
recovering the calcium and/or magnesium salt of acetic acid from the aqueous phase.

11. A process for producing calcium and/or magnesium salts of acetic acid comprising the following steps:
pretreating biomass to facilitate fermentation;
fermenting the biomass anaerobically in a continuous manner to form acetic acid in a fermentation broth;
extracting the acetic acid continuously from the fermentation broth with an oil phase which may optionally contain a liquid ion exchanger, resulting in the production of an organic phase consisting essentially of oil, acetic acid and optionally, a liquid ion exchanger material;
treating the acetic acid-containing organic phase directly and continuously with water and solid basic material containing calcium and/or magnesium metal ions, resulting in the formation of calcium and/or magnesium salt of acetic acid and water, the water forming an aqueous phase, the acetic acid salt being located substantially in the aqueous phase;
reacting the oil phase and the water phase with hydrated lime thereby utilizing any previously unreacted acetic acid and enhancing the production acetic acid salt; and
recovering the calcium and/or magnesium salt of acetic acid from the aqueous phase.

12. A process for producing a metal salt of acetic acid comprising the following steps:
fermenting biomass anaerobically in a continuous manner to form acetic acid in a fermentation broth;
extracting the acetic acid continuously from the fermentation broth with an oil phase which may optionally contain a liquid ion exchanger, resulting in the production of an organic phase consisting essentially of oil, acid, and optionally, a liquid ion exchanger material;
treating the acetic acid-containing organic phase directly and continuously with solid basic material containing metal ions, resulting in the formation of said metal salt of acetic acid and water, the water forming an aqueous phase, the acetic acid salt being located substantially in the aqueous phase; and
removing said metal salt of acetic acid from the aqueous phase.

* * * * *

UNITED STATES PATENT AND TRADEMARK OFFICE
CERTIFICATE OF CORRECTION

PATENT NO. : 5,254,465
DATED : October 19, 1993
INVENTOR(S) : Donald L. Wise

It is certified that error appears in the above-indentified patent and that said Letters Patent is hereby corrected as shown below:

On the title page, item [54] and column 1, line 3, insert --METAL-- after "EARTH".

On the title page, item [57], in the Abstract, line 1, "earth salts" should read --earth metal salts-- and line 8, "earth acetate" should read --earth metal acetate--.

Column 3, line 54, "carboxylio" should read --carboxylic--.

Column 8, line 49/50, "fossil fuels consisting of coal bituminous, subbituminous, lignite, and peat;" should read --bituminous coal, subbituminous coal, lignite, and peat;--.

Column 10, line 17, "a metal salt" should read --an alkaline earth metal salt--.

Column 10, line 29, "containing metal" should read --containing alkaline earth metal--.

UNITED STATES PATENT AND TRADEMARK OFFICE
CERTIFICATE OF CORRECTION

PATENT NO. : 5,254,465
DATED : October 19, 1993
INVENTOR(S) : Donald L. Wise

It is certified that error appears in the above-indentified patent and that said Letters Patent is hereby corrected as shown below:

Column 10, line 30, "said metal" should read --said alkaline earth metal--.

Column 10, line 33, "said metal salt" should read --said alkaline earth metal salt--.

Signed and Sealed this

Twenty-third Day of August, 1994

Attest:

BRUCE LEHMAN

Attesting Officer        Commissioner of Patents and Trademarks